(12) United States Patent
Goyal et al.

(10) Patent No.: US 12,402,889 B2
(45) Date of Patent: Sep. 2, 2025

(54) HEMOSTASIS AIDING DEVICE

(71) Applicant: Sandeep Kumar Goyal, Atlanta, GA (US)

(72) Inventors: Sandeep Kumar Goyal, Atlanta, GA (US); John Homer Tipton, Marietta, GA (US); Emily Sara Blum, Atlanta, GA (US)

(73) Assignee: Sandeep Kumar Goyal, Atlanta, GA (US)

( * ) Notice: Subject to any disclaimer, the term of this patent is extended or adjusted under 35 U.S.C. 154(b) by 492 days.

(21) Appl. No.: 17/894,877

(22) Filed: Aug. 24, 2022

(65) Prior Publication Data

US 2023/0061344 A1 Mar. 2, 2023

Related U.S. Application Data

(60) Provisional application No. 63/236,437, filed on Aug. 24, 2021.

(51) Int. Cl.
*A61B 17/132* (2006.01)
*A61B 17/00* (2006.01)
*A61B 17/04* (2006.01)
*A61B 17/12* (2006.01)

(52) U.S. Cl.
CPC ...... *A61B 17/1325* (2013.01); *A61B 17/0487* (2013.01); *A61B 2017/00946* (2013.01); *A61B 2017/12004* (2013.01)

(58) Field of Classification Search
CPC ............ A61B 17/1325; A61B 17/0487; A61B 17/135; A61B 17/1355; A61B 17/1322; A61B 17/132; A61B 17/1327; A61B 2017/00946; A61B 2017/12004; A61B 2017/00659; A61B 2017/00663; A61B 2017/00964
USPC ........................................................ 606/153
See application file for complete search history.

(56) References Cited

U.S. PATENT DOCUMENTS

| | | | |
|---|---|---|---|
| 2010/0179586 A1* | 7/2010 | Ward | A61B 17/135 606/202 |
| 2015/0119926 A1* | 4/2015 | Saatchi | A61B 17/1325 606/202 |
| 2015/0305958 A1* | 10/2015 | Hoff | A61B 17/1325 601/134 |
| 2018/0014831 A1* | 1/2018 | Salimi | A61B 17/135 |
| 2019/0167273 A1* | 6/2019 | Morrison | A61B 17/135 |

* cited by examiner

*Primary Examiner* — Jocelin C Tanner
(74) *Attorney, Agent, or Firm* — Smith Gambrell & Russell LLP

(57) ABSTRACT

A hemostasis aiding device for use at wound sites associated with venous access procedures.

21 Claims, 8 Drawing Sheets

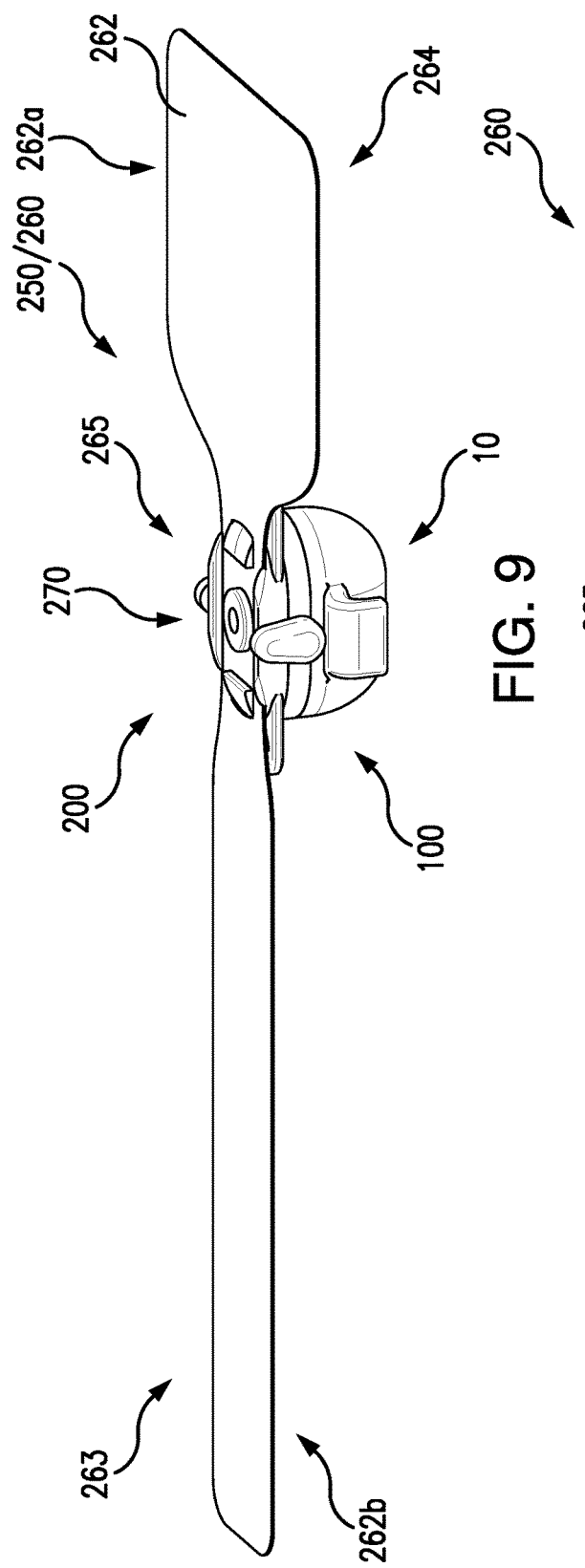
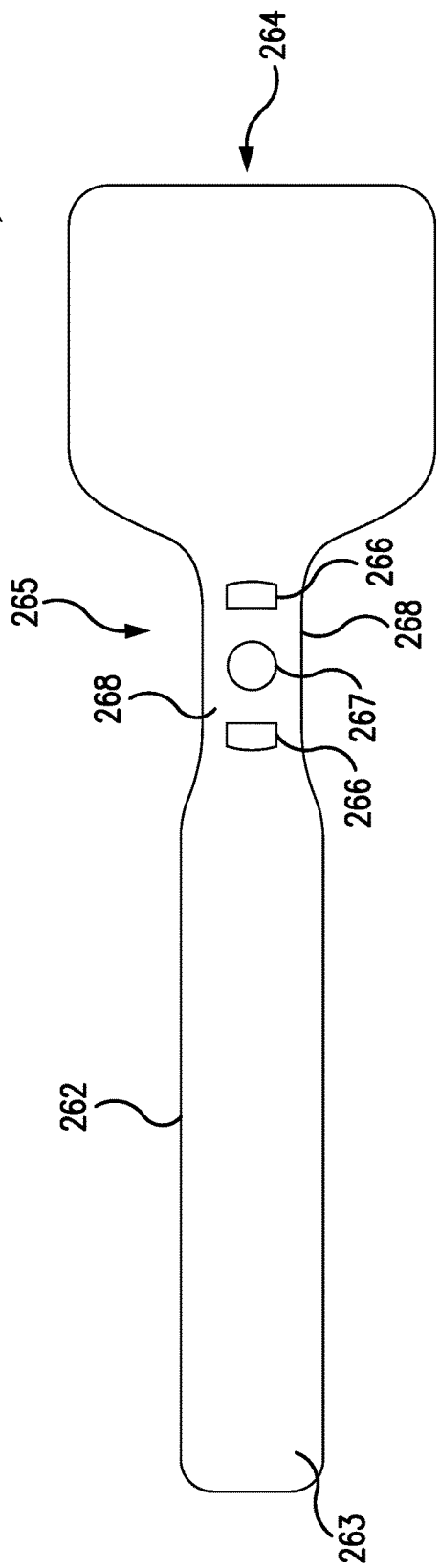

HEMOSTASIS AIDING DEVICE

CROSS-REFERENCE OF RELATED APPLICATIONS

This application claims priority to U.S. Provisional Application No. 63/236,437, filed Aug. 24, 2021, the entirety of which is incorporated by reference herein.

FIELD OF INVENTION

This invention generally relates to hemostasis aiding devices for use with wounds made in endovascular procedures.

BACKGROUND OF THE INVENTION

Many various procedures require vascular access, which creates a puncture wound that eventually will need to be closed. After the process is completed, steps must be taken to close the wound. Wound closure typically involves compression to control bleeding until hemostasis occurs. Ideally, wound closure serves to minimize blood loss, effect hemostasis, and render the patient ambulatory in a relatively short period of time.

Traditionally, wound closure has been a manual operation where a physician or trained clinician used manual hand pressure, using either one or two hands. This is the gold standard for wound closure. However, such a process is time consuming, requiring a physician or trained clinician to apply pressure for at least 30 minutes, while also requiring a patient lie completely flat for several hours. There are additional problems as well. For example, manual pressure that is too firm does not allow sufficient clotting factors to accumulate and can potentially occlude blood flow completely. Moreover, manual pressure could be applied unevenly: the person exerting manual pressure can tire, or the fingers may move or may not be placed properly. The person may also stop the application of pressure to examine the wound, causing a disruption of the maturing clot.

In response to these problems, various specialized vascular closure devices (VCDs) have been proposed. However, they have not fully solved the problems inherent in wound closures. Accordingly, there is an unfulfilled need in the art for a simple-to-use VCD which closely mimics "gold standard" manual wound closure.

SUMMARY OF THE INVENTION

The invention is directed at a hemostasis aiding device. In an aspect, the hemostasis aiding device includes a pressure applying system and a securing system. A main body can connect the pressure applying system to the securing system. The pressure applying system can include a malleable patient pressure subsystem and a non-malleable patient-pressure subsystem. In such aspects, the main body supports both the malleable and non-malleable patient pressure subsystem and the non-malleable subsystems.

In an aspect, the malleable patient pressure subsystem includes a silicone bulb portion. The silicone bulb portion can include a stabilization portion and a pressure point. In an aspect, the non-malleable patient pressure subsystem applies force to the pressure point of the silicone bulb.

The pressure applying system can include a suture securing subsystem and an external securing subsystem. The suture securing subsystem includes an interior channel to receive a suture and a suture locking mechanism to lock the hemostasis aiding device to the suture connected to a patient. The external securing subsystem can include an adhesive subsystem and a strap subsystem.

The accompanying drawings are included to provide a further understanding of the invention and are incorporated in and constitute part of this specification, as well as illustrate several embodiments of the invention that together with the description serve to explain the principles of the invention.

BRIEF DESCRIPTION OF THE FIGURES

FIG. 9 is a perspective view of the hemostasis aiding device on a securing mechanism according to an aspect of the present invention.

FIG. 10 is a top plan view of the securing mechanism of FIG. 9.

DETAILED DESCRIPTION OF THE INVENTION

Embodiments of the invention will be described more fully hereinafter with reference to the accompanying drawings, in which embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art.

In the following description, numerous specific details are set forth. However, it is to be understood that embodiments of the invention may be practiced without these specific details. In other instances, well-known methods, structures, and techniques have been shown in detail in order not to obscure an understanding of this description.

Figure 1:
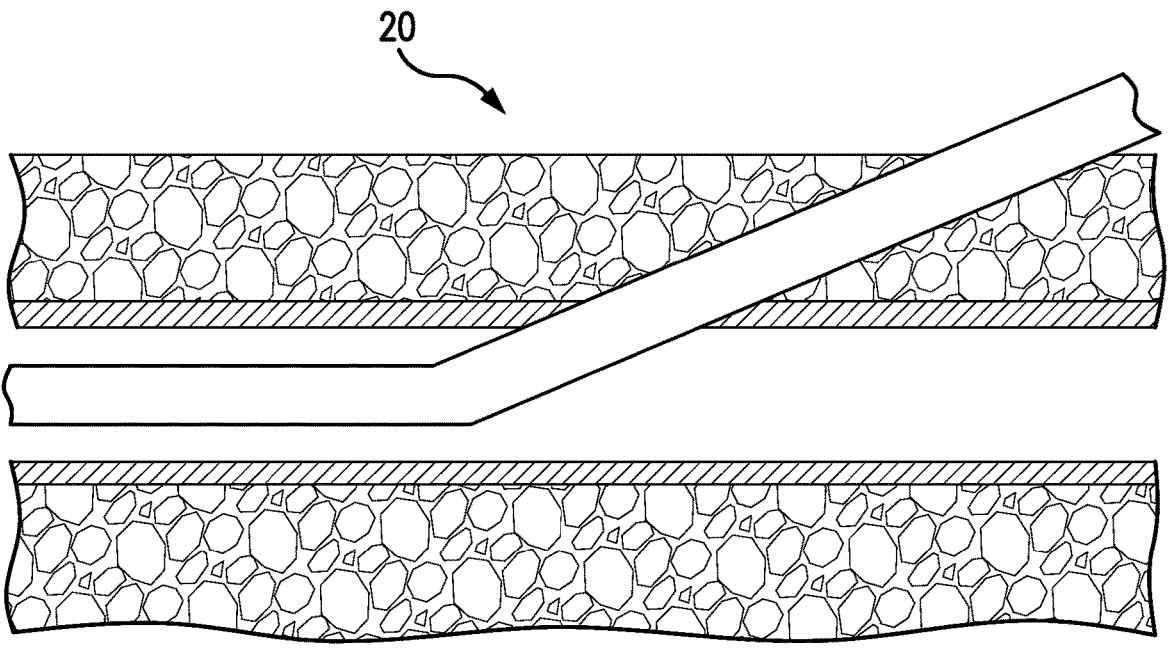
FIG. 1 is a schematic representation of a placement of an access sheath. Subcutaneous tissues contain small ovals for differentiation and the vasculature is lined with crosshatching.
Figure 2:
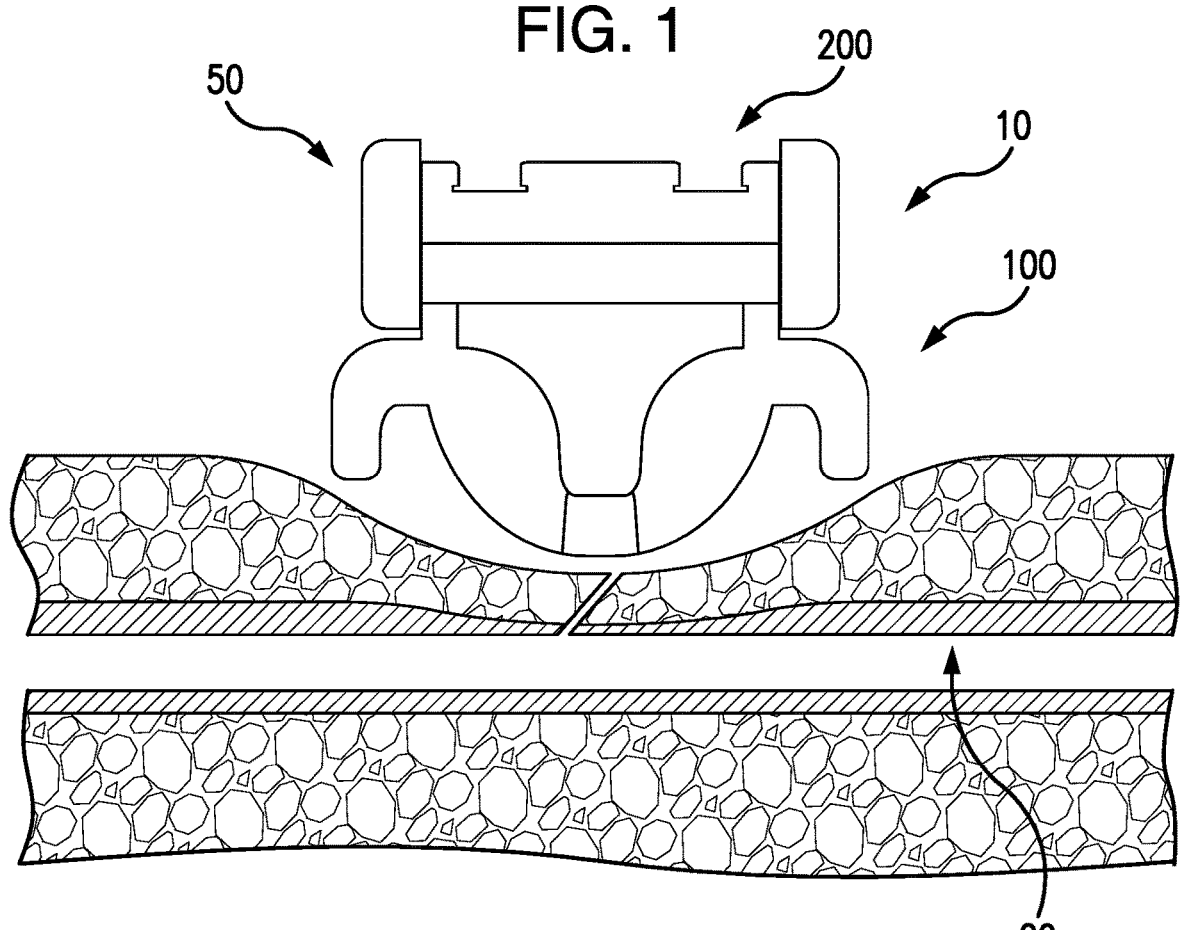
FIG. 2 is a schematic representation of the hemostasis aiding device applied to the wound area of FIG. 1 according to an aspect of the present invention.
Figure 3:
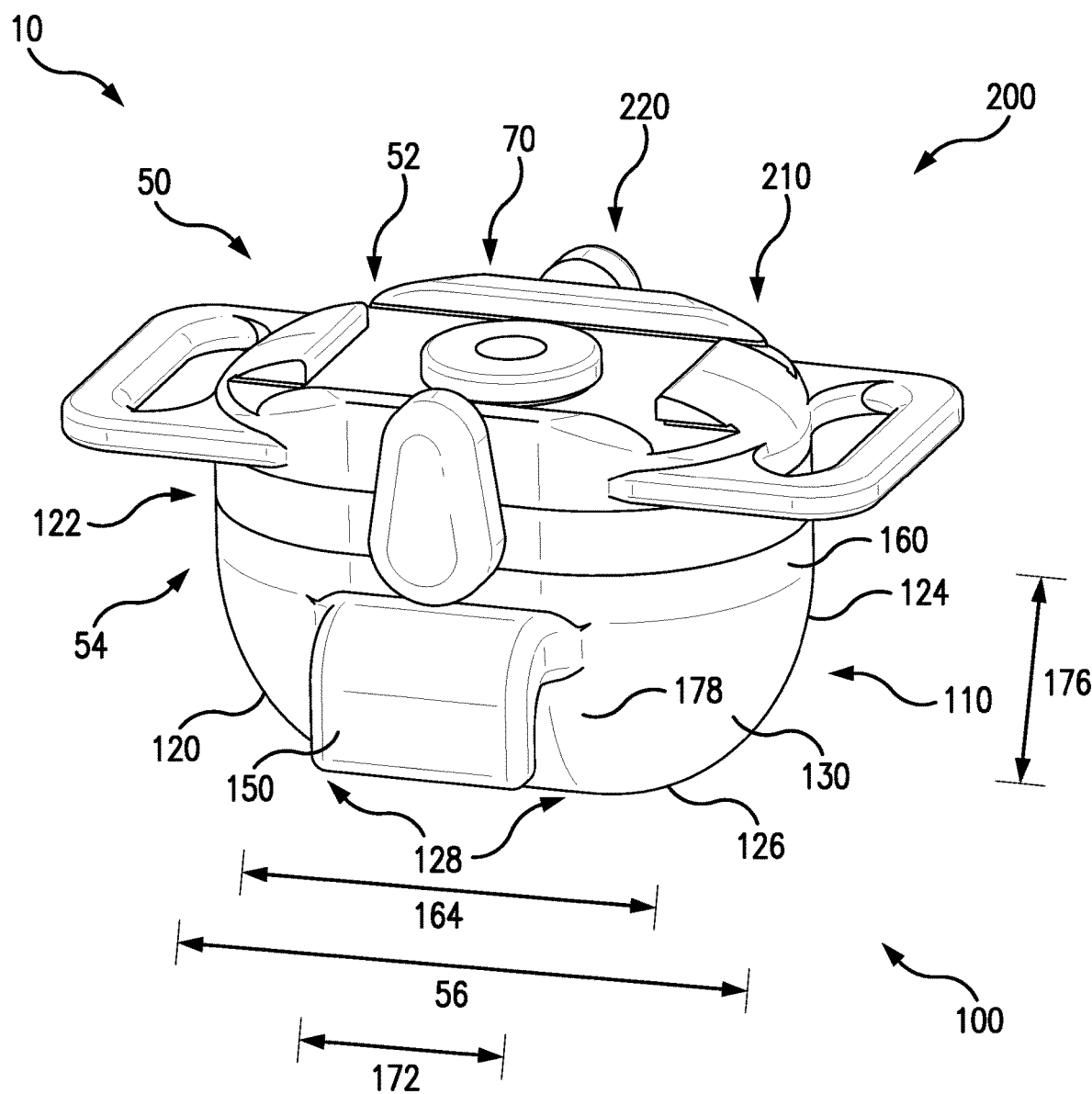
FIG. 3 is a perspective view of the hemostasis aiding device according to an aspect of the present invention.
Figure 4:
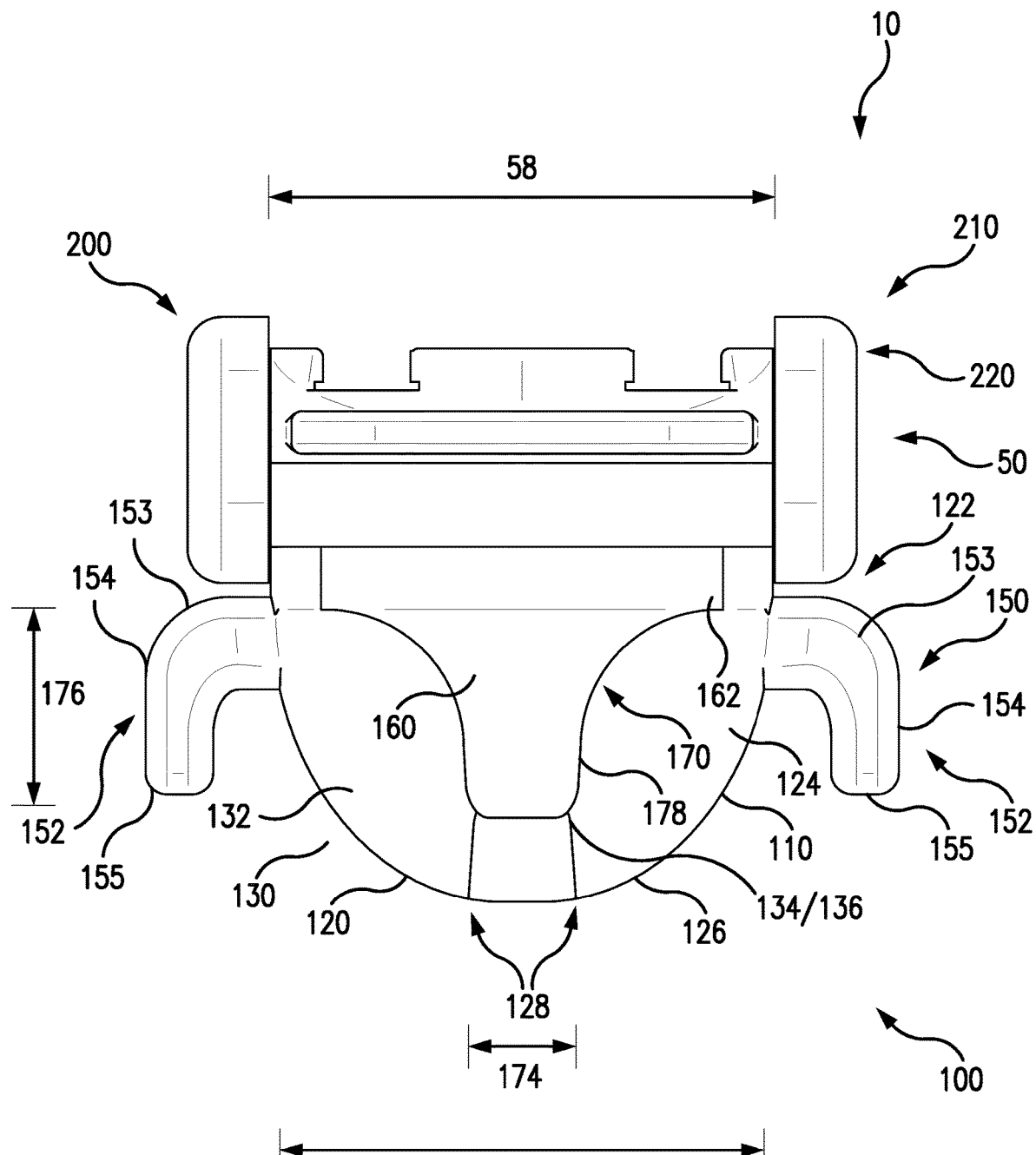
FIG. 4 is a front plan view of the hemostasis aiding device of FIG. 3.
Figure 5:
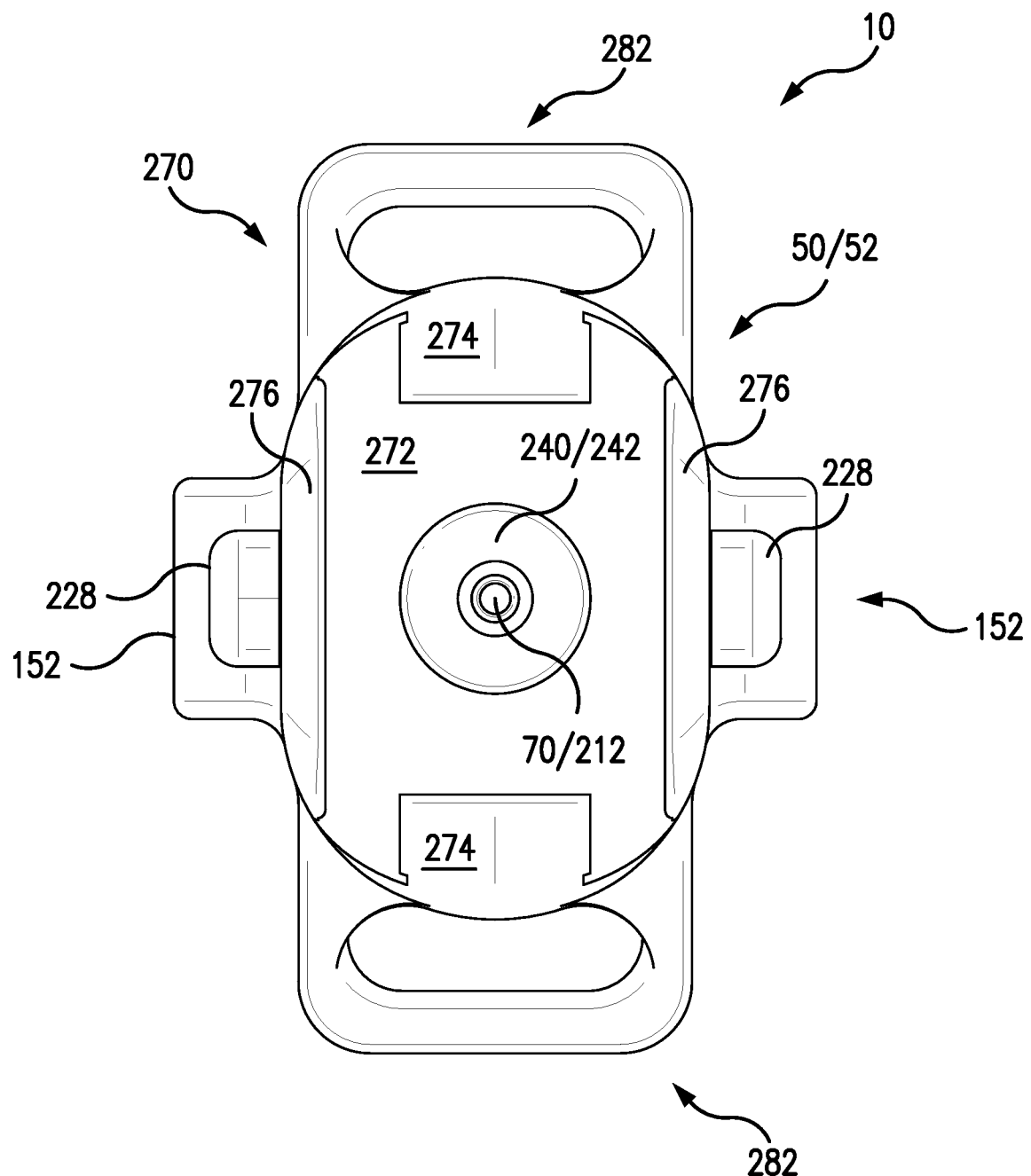
FIG. 5 is a top plan view of the hemostasis aiding device of FIG. 3.
Figure 6:
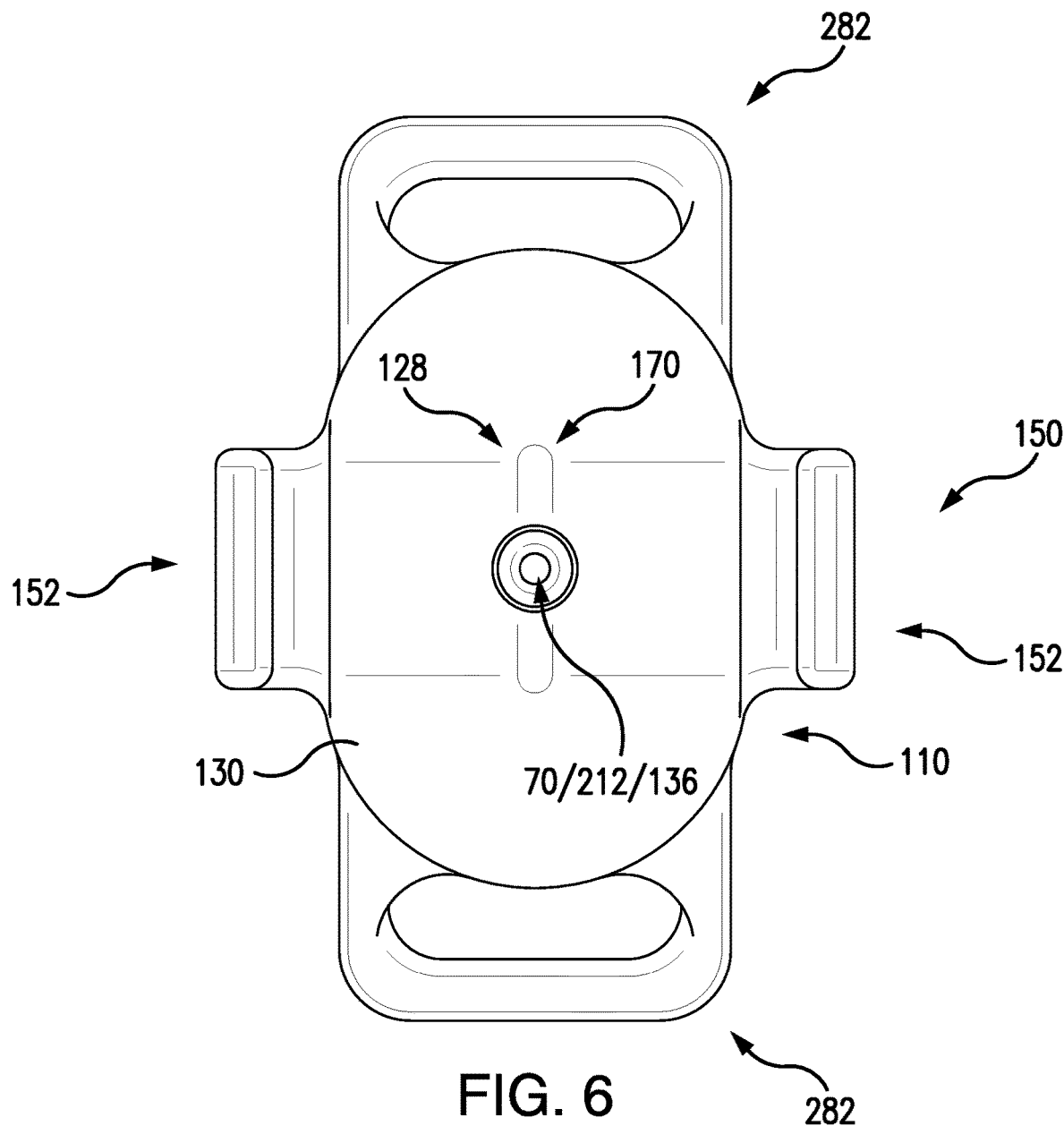
FIG. 6 is a bottom plan view of the hemostasis aiding device of FIG. 3.

In an aspect, the invention is directed at a hemostasis aiding device 10, as shown in FIGS. 2-10. The hemostasis aiding device 10 is intended to aid in achieving hemostasis after a procedure that required femoral venous access, as shown in FIGS. 1-2. Similar/related procedures include catheter based cardiac ablation, transcatheter mitral valve replacement, catheter hemodialysis, and venous-arterial ECMO catheterizations. The device 10 works by applying pressure to the wound site 20 after the procedure. This site 20 is typically located in the groin crease. However, other areas of use include, but are not limited to, the arm. While it is possible to utilize the hemostasis aiding device 10 after procedures that required arterial and/or venous access, the device 10 is intended for use with venous applications given the lower level of blood pressure through veins in comparison to arteries.

Using this device 10 reduces post-operative recovery time, and also the bedside attendance of a caretaker, and improve patient comfort. That is, the device 10 applies the needed pressure to stop the bleeding without the need of additional pressure applying sources (e.g., clinician). In an aspect, the device 10 is equivalent to the gold standard of hemostasis, which is to have a clinician use manual closure and/or apply pressure until bleeding is stopped. Assuming complete device success, the gold standard intervention requires 10-20 minutes for first hemostasis and a repeat of that procedure/time if the clotting fails.

In an aspect, the device 10 is configured to be used as a single use sterile device 10. However, in other aspects, components of the device 10 can be configured for multiple uses. As shown, the hemostasis aiding device 10 includes a main body 50 supporting a pressure applying system 100 and a securing system 200. The pressure applying system 100 applies pressure directly to the wound area 20 to assist with hemostasis. The securing system 200 secures the pressure applying system 100 to the wound site 20, but also assists in applying pressure via the pressure applying system 100, as discussed below.

In an aspect, the main body 50 is integrated with both the pressure applying system 100 and the securing system 200. In such instances, the main body 50 can share features of the applying system 100 and the securing system 200. The main body 50 includes a top surface 52 and a bottom surface 54. In an aspect, the pressure applying system 100 is coupled/formed on the bottom surface 54, and the securing system 200 is coupled to/formed on portions of the top surface 52. In an aspect, the main body 50 has a length 56 and a width 58. In an aspect, the main body 50 can have an oblong shape, with the length 56 being greater than the width 58. In such aspects, components of the pressure applying system 100 can share the general oblong shape, as discussed below. The main body 50 can also include an aperture 70, discussed below.

The pressure applying system 100 can include a malleable portion 110 and a non-malleable portion 160. The malleable portion 110 can include a malleable bulb 120. In such aspects, the malleable bulb 120 is configured to be malleable, but capable of applying pressure to a wound area 20. In an aspect, the malleable bulb 120 is made of a deformable material that is capable of transferring some force to the wound area without causing the subject pain or irritation. In an aspect, the deformable material is silicone, but in other aspects other deformable materials can be utilized. However, it is preferred that the material be capable of being sterilized as well as not cause skin irritation. Further, the malleable bulb 120 can be configured to be hollow, which aids in the deformity/malleability of the bulb 120. Further, in such aspects, the bulb 120 being hollow provides a location for the non-malleable portion 150 to be housed, as discussed below.

The hollow malleable bulb 120 includes a top 122, side walls 124 that extend from the top 122 to a bottom 126 that includes a pressure point 128 (discussed below), forming an exterior surface 130, and an interior surface 132. In an aspect, protrusions/tabs can be found along the top 122 of the interior surface 132 that correspond to matching securing pockets 60 found on the bottom of the main body 50. This protrusion/securing pockets interface, couples, and retains the malleable bulb 120 to the main body 50.

In an aspect, the top 122 of the bulb 120 matches the oblong profile shape of the main body 50, with the side walls 124 extending towards the bottom 126 in a rounded fashion. The curved nature of the bottom 126 forms the pressure point 128 on the exterior surface 130 of the bulb 120 that is configured to engage the skin of the wound site 20 and apply pressure. Extending upwards from the interior surface 132 of the bulb 120 is a connecting member 134 that is configured to engage the non-malleable portion 150, discussed below. In an aspect, the connecting member 134 includes an aperture/channel 136.

Given that the malleable bulb 120 is malleable as pressure is applied, it is possible that the pressure point 128 could move from the desired location, or that the bulb 120 is deformed and decreases the amount of pressure applied at the wound site 20. To prevent this, the malleable portion 110 includes a stabilization subsystem 150. The stabilization subsystem 150 is configured to keep the pressure point 128 of the malleable bulb 120 at the right location at the wound site 20 and in an orientation that maintains the desired amount of pressure at the wound sight/pressure point interface.

In an aspect, the stabilization subsystem 150 includes a pair of stabilization wings 152. These stabilization wings 152 can extend from the sidewalls 124 on the exterior surface 130 of the malleable bulb 120 at opposite positions. In such aspects, the stabilization wings 152 are malleable as well, and made from the same material as the malleable bulb 120 and integrated into the side walls 124. However, in other aspects, the stabilization wings 152 can be detachable. In an aspect, the stabilization wings 152 include a horizontal portion 153 that extends from the side walls 124, and a vertical portion 154 that extend downward from ends of the horizontal portions 153 opposite the side walls 124. In an aspect, the vertical portions 154 include edges 155 that are configured to engage the skin of the subject adjacent the wound site 20. As the stabilization wings 152 provide support while the malleable bulb 120 applies pressure to the wound pressure and becomes depressed, the edges 155 are found on a plane above the plane of the bottom 126/pressure point 128 of the bulb 120. In other words, the bulb 120 has to be depressed before the edges 155 engage the skin of the subject.

As discussed above, the malleable portion 110 works with the non-malleable pressure applying portion 160 to apply pressure to the wound. The non-malleable pressure applying portion 160 includes a base 162 that is attached to/integrated the bottom surface 54 of the main body 50. In an aspect, the base 162 can house the securing pockets 60. The base 162 has a length 164 and a width 166. The shape of the base 162 can correspond to the shape of the main body 50. For example, the base 162 can have an oblong shape that corresponds to the oblong shape of the main body, with the length 164 being greater than the width 166.

A tapered member 170 can extend away from the base 162. The tapered member 170 has a length 172, width 174, and a depth 176, with the length 172 and the width 174 decreasing in the depth 176 direction. A bottom 178 is found at the end of the tapering member 170 opposite the base 162. As discussed above, the non-malleable portion 160 can be housed within the hollow malleable bulb 120, with the bottom 178 of the tapered member 170 engaging the interior protrusion 134 of the interior surface 130 of the bulb 120. The non-malleable pressure applying portion 160 is configured to apply pressure only after the malleable portion 110 has begun to substantially apply pressure. In other words, the malleable bulb 120 has applied pressure and is being deformed before the bottom 178 of the tapered member 170 begins to apply pressure. In addition, the non-malleable portion 160 provides additional stabilization. The tapered member 170 can include an aperture 180 that extends through its body and is in alignment with the aperture 136 of the bulb 120.

Figure 8:
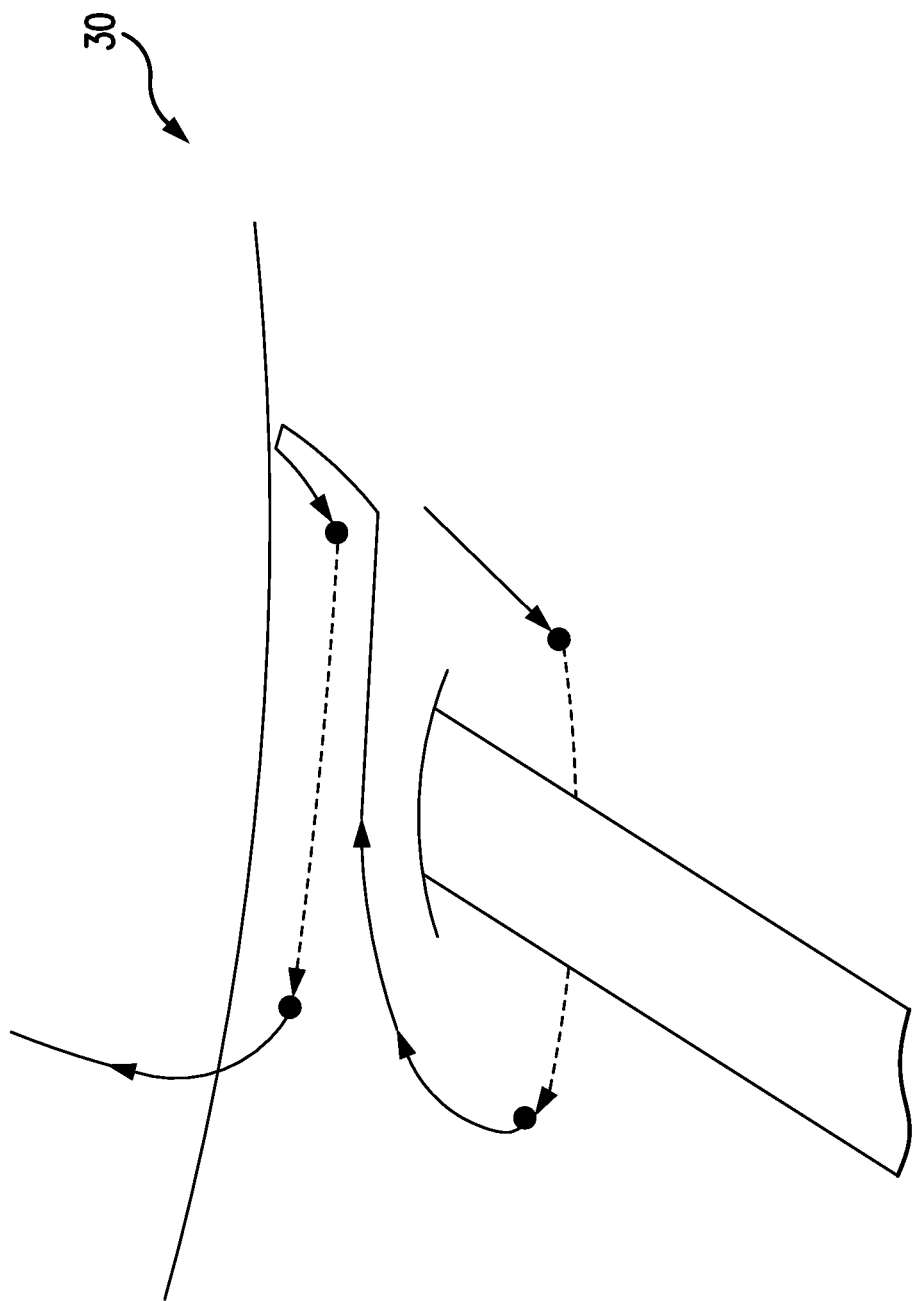
FIG. 8 is a schematic illustration of a suture utilized by a hemostasis aiding device according to an aspect of the present invention.

The pressure applying system 100 works with the securing system 200 to ensure that pressure is applied correctly to the wound site 20. In an aspect, the securing system 200 can include a suture securing subsystem 210 and an external securing subsystem 250. In an aspect, the suture securing subsystem 210 works with a suture 30 applied at the wound site 20. For example, a Z-suture 30 as shown in FIG. 8 can be utilized. Various materials can be used for the suture 30. In an aspect, a 2-0 Ethibond suture 30 on a CT-1 needle can be utilized. However, other sutures, materials and shape, can be utilized. In various types, the suture 30 should not be knotted, but secured by the device, as discussed below.

The suture securing subsystem 210 receives the suture 30 via an interior channel 212. The interior channel 212 extends through multiple components of the device 10, formed from the aperture 136 of the bulb 120, the aperture 180 of the tapered member 170, and the aperture 70 of the main body 50. The suture securing subsystem 210 also includes a suture locking mechanism 220. The suture locking mechanism 220 can be found within the interior of the main body 50. The suture locking mechanism includes a rotating member 222 housed within a horizontal locking channel 230. The rotating member 222 can include a spherical portion 224. The spherical portion 224 includes an aperture 226 that forms part of the interior channel 212. The locking channel 230 includes a corresponding spherical hollow portion 232 that houses the spherical portion 224 of the rotating member 222. Knobs 228 can be found at the ends of the rotating member 222 which allows a physician or medical professional to rotate the rotating member 222.

The suture securing subsystem 210 includes a mount extension 240 found on the top surface 52 of the main body 50. The mount extension 240 is raised above the top surface 52 of the main body 50, and includes a flange 242. In an aspect, the flange 242 has a circular shape. The mount extension 240 includes an aperture 244 that is part of the interior channel 212.

The suture securing subsystem 210 works with the external securing subsystem 250. The external securing subsystem 250 can be configured to apply the needed force to help hemostasis at the wound site 20. In an aspect, the external securing subsystem 250 can include an adhesive subsystem 260 and/or a strap subsystem 280.

In an aspect, the adhesive subsystem 260 includes an adhesive strap 262 and a mounting component 270. The adhesive strap 262 includes a top surface 262a and an adhesive bottom surface 262b. The adhesive strap 262 includes an elongated portion 263, a fat portion 264, and a mount portion 265 connecting the elongated portion 263 to the fat portion 264. The mount portion 265 matches the shape of the mount component 270. As shown, the mount portion 265 includes notch apertures 266 and a flange aperture 267, and edges 268, discussed below. In other aspects, the adhesive strap 262 can have portions of different size and shapes dependent on the location of the wound to be addressed. For example, the adhesive strap 262 as shown in FIGS. 9-10 is shaped accordingly to avoid a long strap on the inner side so it does not encroach on a middle part of the pelvic area when used on a wound associated with femoral venous access.

Figure 7:
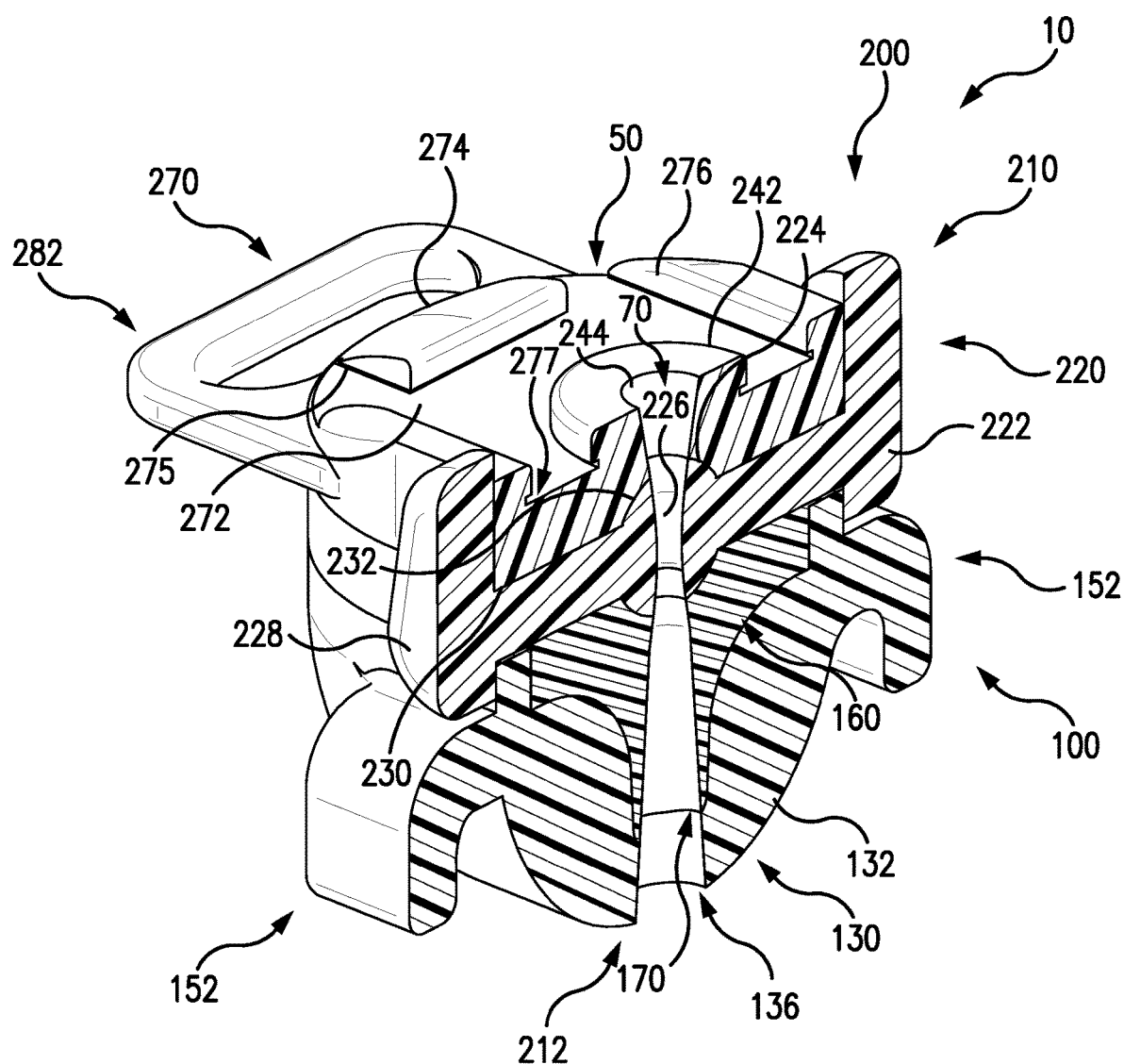
FIG. 7 is a cross-sectional view of the hemostasis aiding device of FIG. 3.

The mount component 270 is configured to receive the adhesive strap 262 at the mount portion 265. The mount component 270 is found on top surface 52 of the main body 50 of the device 10. The mount component 270 includes a combination of tabs, nooks, and side members to secure the adhesive strap 262. As shown in FIG. 7, the mount component 270 includes the mount extension 240 with its flange 242, an inlet 272 with tabs 274 and side members 276. The tabs 274 and side securing members 276 can both include notches 275, 277, respectively, that engage the notch apertures 266 and edges 268 of the adhesive strap 262, with the flange 242 also securing the flange aperture 267.

The strap subsystem 280 can include d-rings 282 found on the main body 50. A Velcro strap (not shown) can be utilized with the d-rings 282 to secure the main body 50, and the pressure system 100, to the patient. In various aspects, the adhesive subsystem 260 and the strap subsystem 280 can come in various lengths and sizes to accommodate the different sizes of patients and limbs.

To apply the device 10, a suture 30 (e.g., FIG. 8) is made at the wound site 20. The ends of the suture 30 are then fed through the interior channel 212, starting at the aperture 136 of the bulb 120 and then pulled through the aperture 70 of the main body 50. Once it is pulled through, the end of the suture 30 is then wrapped around the mount extension 240 and the suture locking mechanism 220 is engaged by turning the knobs 228. As the knobs 228 are turned, the rotating member 222 is rotated. The edges of the aperture 226 of the spherical member 224 engage the suture 30, and pull it tighter within the spherical hollow 232 of the horizontal channel 230. This "locks" the device 10 on the suture 30 at the right location. In an aspect, the rotating member 222 rotates 90 degrees to facilitate a user friendly binary lock or unlock. However, in other aspects, the rotating member 222 can have an infinite rotation that allows the user to draw-up the suture 30 to provide extra tension.

From here, the external securing subsystem 250 is utilized which may utilize either the adhesive subsystem 260 or strap subsystem 280 to further secure the device 10 to the subject. If the adhesive subsystem 260 is utilized, the mount portion 265 of the adhesive strap 262 is placed within the mount component 270 of the main body 50, with the tabs 274 being fed into the notch apertures 266, with their notches engaging the notch aperture 266, the flange 242 into the flange aperture 267, and the edges 268 placed within the notches 277 of the side securing members 276. From here, the elongated portion 263 and the fat portion 264 are tightened and adhered to the surface of the subject's skin near the wound site 20. The adhesive subsystem 260 can be pulled taught to apply more pressure. If the strap subsystem 280 is utilized, a Velcro strap is fed through the d-rings 282 and then tightened.

In either case, when the external securing subsystem 250 is engaged, pressure is applied to the device 10, which activates the pressure applying system 100, including both the malleable and non-malleable portions 110, 160. The pressure point 128 of the malleable bulb 120 is pressed against the wound surface. As the bulb 120 is deformed, the stabilizing subsystem 150 is engaged, with the wings 152 keeping the pressure point 128 in place. At the same time, the non-malleable portion 160 applies pressure to the pressure point 128. The securing system 200 remains engaged until hemostasis occurs.

The device 10 discussed above produces a force that substitutes for the needed force applied by a physician or nurse. For example, the pressure applied by the hemostasis aiding device 10 over a number of trials was between 8 and 14 Newtons with the true average being ~12 N, which is enough force to translate pressure through potentially thick tissue to the venous site. In addition, the device 10 can be applied fairly quickly. Device placement with the sheet adhesive took between 13 and 30 seconds (20 second average) without the suture. If a suture is being used (not including suture placement time) the time to placement ranged from 22-70 seconds with the average approximately 42 seconds.

Having thus described exemplary embodiments of the present invention, it should be noted by those skilled in the art that the disclosures are exemplary only and that various other alternatives, adaptations, and modifications may be made within the scope of the present invention. Accordingly, the present invention is not limited to the specific embodiments as illustrated herein, but is only limited by the following claims.

What is claimed is:

1. A hemostasis aiding device for use with a subject after a venous access procedure, the device comprising:
   a. a securing system to secure the hemostasis aiding device proximate a wound site; and
   b. a pressure applying system to apply pressure to the wound site of the venous access procedure of the subject, wherein after the hemostasis aiding device is secured to the subject, the pressure applying system is configured to apply pressure without additional pressure applying sources, wherein the pressure applying system includes:
      i. a malleable portion configured to engage the wound site, the malleable portion including a pressure point to apply pressure at the wound site;
      ii. a non-malleable portion configured to apply pressure to the malleable portion which applies pressure to the wound site; and
      iii. a stabilization subsystem configured to keep the pressure point at the wound site as pressure is applied, wherein the stabilization subsystem comprises stabilization wings, wherein each of the stabilization wings includes a horizontal portion extending away from the pressure point, a vertical portion extending downwards from the horizontal portion, and an edge for engaging skin of the subject when pressure is applied.

2. A hemostasis aiding device for use with a subject after a venous access procedure, the device comprising:
   a. a pressure applying system comprising:
      i. a main body having an oval shape having a length and a width, wherein the main body is configured to be placed with the length perpendicular to a direction of a vein of the subject;
      ii. a malleable patient pressure interface portion positioned below the main body comprising:
         A. a silicone bulb portion having:
            a. a bottom portion; and
            b. a pressure point, wherein the bottom portion forms a rounded shape to create the pressure point that, when compressed, flexes and presses into skin;
         B. a stabilization portion associated with the malleable patient pressure interface portion comprising;
            a. a pair of stabilization wings, the wings oriented on opposite sides of the silicone bulb, each wing configured to engage the skin of the subject and keep the silicone bulb from rotating when pressure is applied to the hemostasis aiding device; and
         iii. a non-malleable pressure applying portion positioned on a bottom surface of the main body and extending downward within the malleable patient pressure interface portion; and
   b. a subject securing portion configured to secure the device to the patient comprising;
      i. a suture securing component comprising:
         A. a suture receiving portion; and
         B. a suture locking mechanism; and
      ii. an external securing component configured to work with the pressure applying system to apply additional force comprising:
         A. an interface on the pressure applying system; and
         B. a patient interface portion configured to be secured to the subject.

3. The hemostasis aiding device of claim 1, wherein the securing system is oriented above the pressure applying system when the pressure applying system is applying pressure at the wound site.

4. The hemostasis aiding device of claim 3, further comprising a main body having a top surface and a bottom surface, wherein the securing system is coupled to the top surface and the pressure applying system is coupled to the bottom surface.

5. The hemostasis aiding device of claim 4, wherein the main body and the pressure applying system have an oblong shape.

6. A hemostasis aiding device for use with a subject after a venous access procedure, the device comprising:
   a. a securing system to secure the hemostasis aiding device proximate a wound site; and
   b. a pressure applying system to apply pressure to the wound site of the venous access procedure of the subject, wherein after the hemostasis aiding device is secured to the subject, the pressure applying system applies pressure without additional pressure applying sources, wherein the pressure applying system includes:
      i. a malleable portion comprising a silicone bulb; and
      ii. a non-malleable portion comprises a tapered member housed within the malleable portion, wherein the malleable portion is configured to engage the wound site and the non-malleable portion applies pressure through the tapered member after the malleable portion applies pressure to the wound site.

7. The hemostasis aiding device of claim 6, wherein the malleable portion includes a pressure point to apply pressure to the wound site.

8. The hemostasis aiding device of claim 7, wherein the pressure applying system includes a stabilization subsystem configured to keep the pressure point at the wound site as pressure is applied.

9. The hemostasis aiding device of claim 8, wherein the stabilization subsystem comprises stabilization wings.

10. The hemostasis aiding device of claim 9, wherein each of the stabilization wings includes a horizontal portion extending away from the pressure point, a vertical portion extending downwards from the horizontal portion, and an edge for engaging skin of the subject when pressure is applied.

11. A hemostasis aiding device for use with a subject after a venous access procedure, the device comprising:
   a. a securing system to secure the hemostasis aiding device proximate a wound site, the securing system comprising a suture securing subsystem for use with a suture secured at the wound site, the suture securing subsystem comprising:
      i. an interior channel and a suture locking mechanism to receive the suture; and
   b. a pressure applying system to apply pressure to the wound site of the venous access procedure of the subject, wherein after the hemostasis aiding device is secured to the subject, the pressure applying system applies pressure without additional pressure applying sources.

12. The hemostasis aiding device of claim 11, wherein the suture locking mechanism includes a rotating member that receives the suture, wherein when the rotating member is rotated, the suture is locked in place within the suture securing subsystem.

13. The hemostasis aiding device of claim 1 or 6, wherein the securing system comprises a suture securing subsystem for use with a suture secured at the wound site.

14. The hemostasis aiding device of claim 13, wherein the suture securing subsystem comprises an interior channel and a suture locking mechanism to receive the suture.

15. The hemostasis aiding device of claim 14, wherein the suture locking mechanism includes a rotating member that receives the suture, wherein when the rotating member is rotated, the suture is locked in place within the suture securing subsystem.

16. The hemostasis aiding device of claim 1 or 6, wherein the securing system comprises an external securing subsystem configured to apply additional force.

17. The hemostasis aiding device of claim 16, wherein the external securing subsystem comprises an adhesive subsystem and a mounting component, the adhesive subsystem configured to adhere to the subject and to be received by the mounting component, wherein the mounting component is coupled to the pressure applying system.

18. The hemostasis aiding device of claim 1, 2, 11, or 6, wherein after being secured to the subject, the hemostasis aiding device is configured to apply a force of about 8 Newtons to about 14 Newtons.

19. The hemostasis aiding device of claim 1, wherein the wound site is located at a groin crease of the subject.

20. The hemostasis aiding device of claim 1, wherein the malleable portion comprises a silicone bulb.

21. The hemostasis aiding device of claim 20, wherein the non-malleable portion comprises a tapered member housed within the malleable portion, the tapered member applying pressure to the malleable portion after the malleable portion has applied pressure to the wound site.

* * * * *